United States Patent [19]

Wang et al.

[11] Patent Number: 6,133,292

[45] Date of Patent: Oct. 17, 2000

[54] DIARYL-5-ALKYL-5-METHYL-2-(5H)-FURANONES AS SELECTIVE CYCLOOXYGENASE-2-INHIBITORS

[75] Inventors: Zhaoyin Wang; Erich Grimm; Serge Leger, all of Quebec, Canada

[73] Assignee: Merck Frosst Canada & Co., Kirkland, Canada

[21] Appl. No.: 09/174,048

[22] Filed: Oct. 16, 1998

Related U.S. Application Data

[60] Provisional application No. 60/064,409, Oct. 30, 1997.

[51] Int. Cl.[7] .................. A61K 31/443; A61K 31/34; C07D 405/04; C07D 307/58
[52] U.S. Cl. ............. 514/336; 514/473; 546/284.4; 549/323
[58] Field of Search ................. 546/284.4; 549/323; 514/336, 473

[56] References Cited

U.S. PATENT DOCUMENTS 5,474,995  12/1995  Ducharme et al. .................. 514/241
5,840,746  11/1998  Ducharme et al. .................. 514/438

FOREIGN PATENT DOCUMENTS 2 294 879  5/1996  United Kingdom .

WO 95/00501  1/1995  WIPO .
WO 97/14691  4/1997  WIPO .

*Primary Examiner*—Alan L. Rotman
*Attorney, Agent, or Firm*—Richard C. Billups; David L. Rose

[57]  ABSTRACT

The invention encompasses compounds of Formula I as well as a method of treating COX-2 mediated diseases comprising administration to a patient need of such treatment of a non-toxic therapeutically effective amount of a compound of Formula I

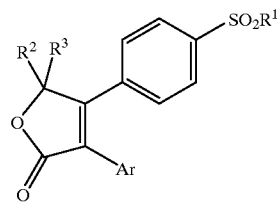

e.g. (5R)-3-(3,4-difluorophenyl)-5-ethyl-5-methyl-4-[4-(methylsulfonyl)phenyl]-2,5-dihydro-2-furanone.

10 Claims, No Drawings

DIARYL-5-ALKYL-5-METHYL-2-(5H)-FURANONES AS SELECTIVE CYCLOOXYGENASE-2-INHIBITORS

CROSS REFERENCE TO RELATED APPLICATIONS

This application is a non-provisional application related to U.S. application Ser. No. 60/064,409 filed on Oct. 30, 1997 priority of which is claimed hereunder.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

The potential utilities of selective cyclooxygenase-2 inhibitors are discussed in John Vane, "Towards a better aspirin" in *Nature*, Vol. 367, pp. 215–216, 1994; Bruno Battistini, Regina Botting and Y. S. Bakhle, "COX-1 and COX-2: Toward the Development of More Selective NSAIDs" in *Drug News and Perspectives*, Vol. 7, pp. 501–512, 1994; and David B. Reitz and Karen Seibert, "Selective Cyclooxygenase Inhibitors" in *Annual Reports in Medicinal Chemistry* James A. Bristol, Editor, Vol. 30, pp. 179–188, 1995.

SUMMARY OF THE INVENTION

The invention encompasses compounds of Formula I as well as a method of treating COX-2 mediated diseases comprising administration to a patient in need of such treatment of a non-toxic therapeutically effective amount of a compound of Formula I.

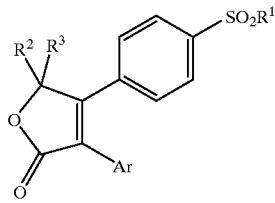

The invention also encompasses certain pharmaceutical compositions for treatment of COX-2 mediated diseases comprising compounds of Formula I.

DETAILED DESCRIPTION OF THE INVENTION

The invention encompasses compounds of Formula I as well as a method of treating COX-2 mediated diseases comprising administering to a patient in need of such treatment a non-toxic therapeutically effective amount of a compound of Formula I

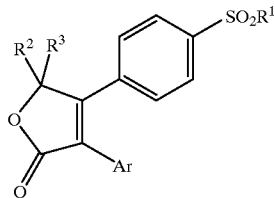

or a pharmaceutically acceptable salt thereof, wherein:
  Ar is an unsubstituted, mono or di substituted phenyl or pyridyl, wherein the substituents are selected from halogen;
  $R^1$ is selected from the group consisting of $NH_2$ and $CH_3$;
  $R^2$ is selected from the group consisting of
    $C_{1-6}$ alkyl unsubstituted or substituted with $C_{3-6}$ cycloalkyl, and
    $C_{3-6}$ cycloalkyl;
  $R^3$ is selected from the group consisting of
    $C_{1-6}$ alkyl unsubstituted or substituted with one, two or three fluoro atoms; and
    $C_{3-6}$ cycloalkyl;
  with the proviso that $R^2$ and $R^3$ are not the same.

In a class of compounds and pharmaceutically acceptable salts of the invention, Ar is unsubstituted phenyl, phenyl substituted with fluoro, or unsubstituted pyrindyl or pyridyl substituted with fluoro.

In a subclass of this class of compounds and pharmaceutically acceptable salts of the invention, $R^2$ is $C_{2-3}$ alkyl, $CH_2$-cyclopropyl, or cyclopropyl.

In a group of this subclass of compounds and pharmaceutically acceptable salts of the invention, $R^3$ is $CH_3$, $CH_2CH_3$ $CH_2F$, $CHF_2$, or $CF_3$.

In a subgroup of this group of compounds and pharmaceutically acceptable salts of the invention, $R^3$ is $CH_3$.

The following abbreviations have the indicated meanings:

| | |
|---|---|
| AA | arachidonic acid |
| Ac | acetyl |
| AIBN | 2.2-azobisisobutyronitrile |
| Bn | benzyl |
| DBU | 1,8-diazobicyclo[5.4.0]undec-7-ene |
| DMAP | 4-(dimethylamino)pyridine |
| DMF | N,N-dimethylformamide |
| DMSO | dimethyl sulfoxide |
| $Et_3N$ | triethylamine |
| HBSS | Hanks balanced salt solution |
| HEPES | N-[2-Hydroxyethyl]piperazine-$N^1$-[2-ethanesulfonic acid] |
| HWB | human whole blood |
| KHMDS | potassium hexamethyldisilazane |
| LDA | lithium diisopropylamide |
| LPS | lipopolysaccharide |
| MMPP | magnesium monoperoxyphthalate |
| Ms | methanesulfonyl = mesyl |
| MsO | methanesulfonate = mesylate |
| NSAID | non-steroidal anti-inflammatory drug |
| OXONE ® | $2KHSO_5$—$KHSO_4$—$K_2SO_4$ |
| PCC | pyridinium chlorochromate |
| PDC | pyridinium dichromate |
| Ph | phenyl |
| r.t. | room temperature |
| rac. | racemic |
| Tf | trifluoromethanesulfonyl = triflyl |
| TfO | trifluoromethanesulfonate = triflate |
| | tetrahydrofuran |
| TLC | thin layer chromatography |
| Ts | p-toluenesulfonyl = tosyl |
| TsO | p-toluenesulfonate = tosylate |
| $SO_2Me$ | methyl sulfone |
| $SO_2NH_2$ | sulfonamide |
| Alkyl group abbreviations | |
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |
| Dose Abbreviations | |
| bid | bis in die (twice daily) |
| qid | quater in die (four times a day) |
| tid | ter in die (three times a day) |

Alkyl, alkenyl, and alkynyl mean linear and branched structures and combinations thereof.

The term "alkyl" means linear and branched structures and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, and the like.

"Cycloalkyl" means a hydrocarbon having the indicated number of carbon atoms, containing one or more rings. Examples of cycloalkyl groups are cyclopropyl, cyclopropylmethyl, 2-cyclohexylethyl, cyclopentyl, cycloheptyl, adamantyl, cyclododecylmethyl, 2-ethyl-1-bicyclo[4.4.0]decyl and the like.

"Fluoroalkyl" means linear and branched alkyl groups and combinations thereof, of the indicated number of carbon atoms, in which one or more hydrogen is replaced by fluorine. Examples are —$CF_3$,—$CH_2CH_2F$, and —$CH_2CF_3$, and the like.

"Fluorocycloalkyl" means a hydrocarbon having the indicated number of carbon atoms, containing one or more rings, in which one or more hydrogen is replaced by fluorine. Examples are c-Pr-$F_5$, c-Pr-$F_5CH_2$, c-Hex-$F_{11}$ and the like.

Halogen includes F, Cl, Br, and I.

Illustrations of the invention are:

(a) 5-ethyl-5-methyl-4-[4-(methylsulfonyl)phenyl ]-3-phenyl-2,5-dihydro-2-furanone, (b) 4-[4-(aminosulfonyl)phenyl ]-5-ethyl-5-methyl-3-phenyl-2,5-dihydro-2-furanone, (c) 5-ethyl-3-(4-fluorophenyl)-5-methyl-4-[4-(methylsulfonyl)phenyl ]-2,5-dihydro-2-furanone, (d) (5S)-5-ethyl-3-(4-fluorophenyl)-5-methyl-4-[4-(methylsulfonyl)phenyl ]-2,5-dihydro-2-furanone, (e) (5R)-5-ethyl-3-(4-fluorophenyl)-5-methyl-4-[4-(methylsulfonyl)phenyl ]-2,5-dihydro-2-furanone, (f) 5-ethyl-3-(3-fluorophenyl)-5-methyl-4-[4-(methylsulfonyl)phenyl ]-2,5-dihydro-2-furanone, (g) 3-(3,4-difluorophenyl)-5-ethyl-5-methyl-4-[4-(methylsulfonyl)phenyl ]-2,5-dihydro-2-furanone, (h) (5R)-3-(3,4-difluorophenyl)-5-ethyl-5-methyl-4-[4-(methylsulfonyl)phenyl ]-2,5-dihydro-2-furanone, (i) (5S)-3-(3,4-difluorophenyl)-5-ethyl-5-methyl-4-[4-(methylsulfonyl)phenyl ]-2,5-dihydro-2-furanone, (j) 4-[4-(aminosulfonyl)phenyl ]-3-(3,4-difluorophenyl)-5-ethyl-5-methyl-2,5-dihydro-2-furanone, (k) 3-(4-chlorophenyl)-5-ethyl-5-methyl-4-[4-(methylsulfonyl)phenyl ]-2,5-dihydro-2-furanone, (l) 3-(4-bromophenyl)-5-ethyl-5-methyl-4-[4-(methylsulfonyl)phenyl ]-2,5-dihydro-2-furanone, (m) 5-methyl-4-[4-(methylsulfonyl)phenyl ]-3-phenyl-5-propyl-2,5-dihydro-2-furanone, (n) 3-(4-fluorophenyl)-5-methyl-4-[4-(methylsulfonyl)phenyl ]-5-propyl-2,5-dihydro-2-furanone, (o) 3-(3-fluorophenyl)-5-methyl-4-[4-(methylsulfonyl)phenyl ]-5-propyl-2,5-dihydro-2-furanone, (p) 3-(3,4-difluorophenyl)-5-methyl-4-[4-(methylsulfonyl)phenyl ]-5-propyl-2,5-dihydro-2-furanone, (q) 4-[4-(aminosulfonyl)phenyl ]-3-(4-fluorophenyl)-5-methyl-5-propyl-2,5-dihydro-2-furanone, (r) 4-[4-(aminosulfonyl)phenyl ]-3-(3,4-difluorophenyl)-5-methyl-5-propyl-2,5-dihydro-2-furanone, (s) 3-(4-fluorophenyl)-5-isopropyl-5-methyl-4-[4-(methylsulfonyl)phenyl ]-2,5-dihydro-2-furanone, (x) 3-(3,4-difluorophenyl)-5-ethyl-4-[4-(methylsulfonyl)phenyl ]-5-(trifluoromethyl)-2,5-dihydro-2-furanone, (y) 3-(3,4-difluorophenyl)-5-ethyl-5-(fluoromethyl)-4-[4-(methylsulfonyl)phenyl ]-2,5-dihydro-2-furanone, (z) 5-(difluoromethyl)-3-(3,4-difluorophenyl)-5-ethyl-4-[4-(methylsulfonyl)phenyl ]-2,5-dihydro-2-furanone, (aa) 5-ethyl-5-methyl-4-[4-(methylsulfonyl)phenyl ]-3-(2-pyridyl)-2,5-dihydro-2-furanone, (bb) 5-ethyl-5-methyl-4-[4-(methylsulfonyl)phenyl ]-3-(3-pyridyl)-2,5-dihydro-2-furanone, (cc) 5-ethyl-5-methyl-4-[4-(methylsulfonyl)phenyl ]-3-(4-pyridyl)-2,5-dihydro-2-furanone, (dd) 5-cyclopropyl-3-(3,4-difluorophenyl)-5-methyl-4-[4-(methylsulfonyl)phenyl ]-2,5-dihydro-2-furanone, and (ee) 5-(cyclopropylmethyl)-3-(4-fluorophenyl)-5-methyl-4-[4-(methylsulfonyl)phenyl ]-2,5-dihydro-2-furanone.

A group of these illustrations includes (c) 5-ethyl-3-(4-fluorophenyl)-5-methyl-4-[4-(methylsulfonyl)phenyl ]-2,5-dihydro-2-furanone, (d) (5S)-5-ethyl-3-(4-fluorophenyl)-5-methyl-4-[4-(methylsulfonyl)phenyl ]-2,5-dihydro-furanone, (e) (5R)-5-ethyl-3-(4-fluorophenyl)-5-methyl-4-[4-(methylsulfonyl)phenyl ]-2,5-dihydro-2-furanone, (f) 5-ethyl-3-(3-fluorophenyl)-5-methyl-4- [4-(methylsulfonyl)phenyl ]-2,5-dihydro-2-furanone, (g) 3-(3,4-difluorophenyl)-5-ethyl-5-methyl-4-[4-(methylsulfonyl)phenyl ]-2,5-dihydro-2-furanone, (h) (5R)-3-(3,4-difluorophenyl)-5-ethyl-5-methyl-4-[4-(methylsulfonyl)phenyl ]-2,5-dihydro-2-furnanone, (i) (5S)-3-(3,4-difluorophenyl)-5-ethyl-5-methyl-4-[4-(methylsulfonyl)phenyl ]-2,5-dihydro-2-furanone, The following compounds are later referred to for carison purposes, but are not compounds of the invention. These compounds are described in (t) 5,5-diethyl-4-[4-(methylsulfonyl)phenyl ]-3-phenyl-2,5-dihydro-2-furanone, (u) 5,5-diethyl-3-(4-fluorophenyl)-4-[4-(methylsulfonyl)phenyl ]-2,5-dihydro-2-furanone, (v) 4-[4-(aminosulfonyl)phenyl]-5,5-diethyl-3-phenyl-2,5-dihydro-2-furanone, (w) 4-[4-(aminosulfonyl)phenyl]-5,5-diethyl-3-(4-fluorophenyl)-2,5-dihydro-2-furanone, In another embodiment, the invention encompasses pharmaceutical compositions for inhibiting COX-2 and for treating COX-2 mediated diseases as disclosed herein comprising a pharmaceutically acceptable carrier and non-toxic therapeutically effective amount of a compound of formula I as described above.

In yet another embodiment, the invention encompasses a method of inhibiting cyclooxygenase and treating cyclooxygenase mediated diseases, advantageously treated by an active agent that selectively inhibits COX-2 in preference to COX- 1 as disclosed herein comprising administering to a patient in need of such treatment of a non-toxic therapeutically effective amount of a compound of Formula I as disclosed herein.

Some of the compounds described herein contain one or more asymmetric centres and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, hydrabamine, N-(2-hydroxyethyl) piperidine, N-(2-hydroxyethyl)pyrrolidine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids. It will be understood that in the discussion of methods of treatment which follows, references to the compounds of Formula I are meant to also include the pharmaceutically acceptable salts.

Compounds of Formula I are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, bums, injuries, following surgical and dental procedures. In addition, these compounds may inhibit cellular neoplastic transformations and metastic tumour growth and hence can be used in the treatment of cancer. The compounds may also be of use in the treatment and/or prevention of cyclooxygenase-mediated proliferative disorders such as may occur in diabetic retinopathy and tumor angiogenesis.

Compounds of the invention will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for treatment of glaucoma.

By virtue of its high inhibitory activity against COX-2 and/or its specificity for COX-2 over COX-1, compounds of the invention will prove useful as an alternative to conventional NSAID'S, particularly where such non-steroidal anti-inflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

For the treatment of any of these cyclooxygenase mediated diseases, compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Similarly, compounds of the invention will be useful as partial or complete substitutes for conventional NSAID'S in preparations wherein they are presently co-administered with other agents of ingredients. Thus in further aspects, the invention encompasses pharmaceutical compositions for treating COX-2 mediated diseases as defined above comprising a non-toxic therapeutically effective amount of compounds of Formula I as defined above and one or more ingredients such as another pain reliever including acetaminophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a prostaglandin including misoprostol, enprostil, rioprostil, ornoprostol or rosaprostol: a diuretic; a sedating or non-sedating antihistamine. In addition the invention encompasses a method of treating cyclooxygenase mediated diseases comprising: administration to a patient in need of such treatment a non-toxic therapeutically effect amount of a compound of Formula I, optionally co-administered with one or more of such ingredients as listed immediately above.

The compounds of the present invention can be prepared according to the following methods.

Method 1

A Friedel-Crafts reaction between an acid chloride 2 and thioanisole 1 yields the substituted acetophenone 3. This acetophenone is hydroxylated to the hydroxyketone 4 using $CCl_4$ and NaOH in toluene with an appropriate phase transfer catalyst (U.S. Pat. No. 4,740,624). Sulfide 4 is oxidized to the sulfone 5 using MMPP or OXONE®. The hydroxyketone 5 is acylated with a phenylacetic acid 6 using a carbodiimide coupling reagent to afford ester 7 which is then cyclised, using a suitable base such as DBU, to the lactone Ia.

Method 2

L-Lactic acid 8 is converted to the dioxolanone 9 with valeraldehyde followed by alkylation using a suitable base such as LDA and an alkylating to give dioxolanone 10 (D. Seebach, N. Reto, G. Calderari, *Tetrahedron* 40, 1313 (1984)). Addition of aryl lithium 11 to dioxolanone 10 afforded dioxolanol 12. Acid catalyzed hydrolysis of the acetal followed by OXONE® oxidation of the methyl sulfide give the hydroxyketone 13(R). The hydroxyketone 13(S) can be prepared according to the method previously described in World Patent Application WO9714691 (1997.04.24), Example 144 steps 1 to 8.

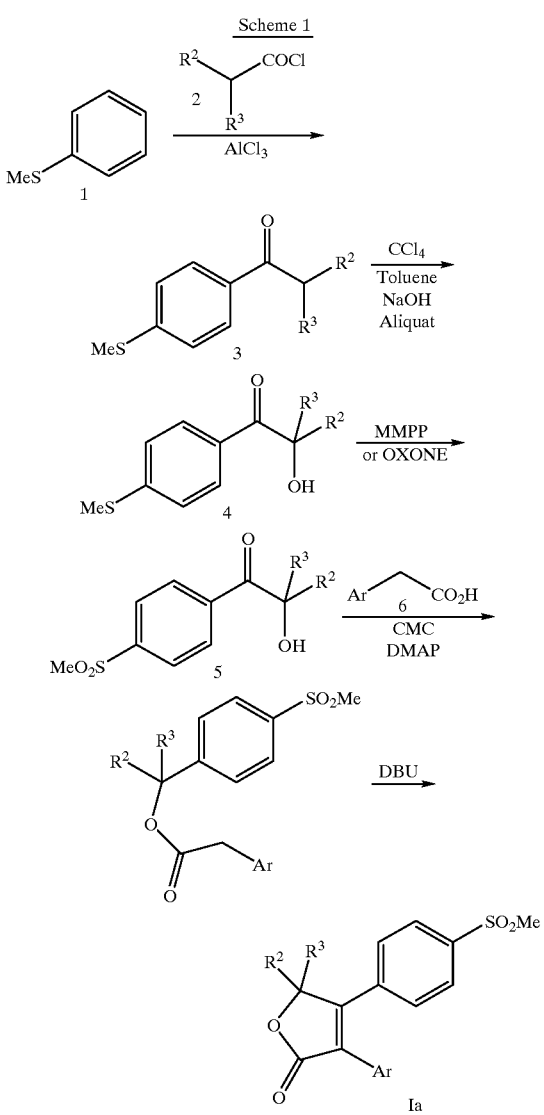

Scheme 1

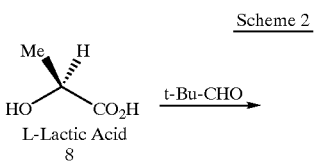

Scheme 2

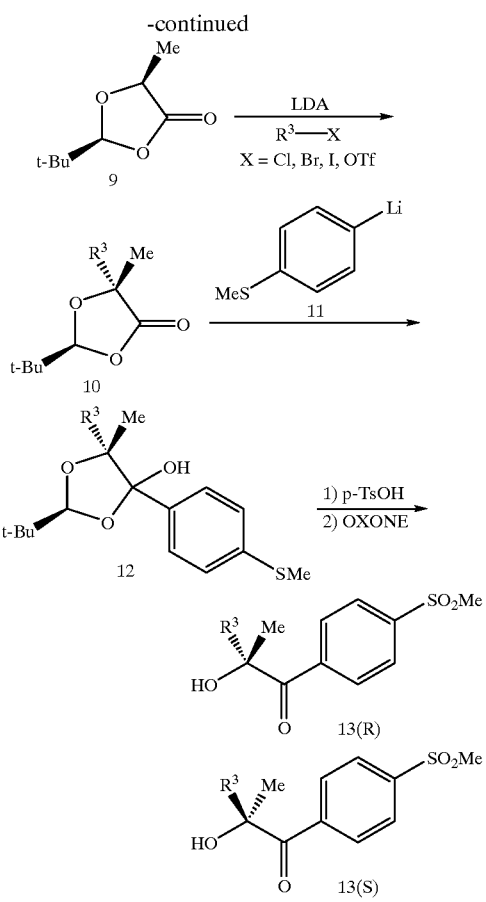

Table 1 illustrates compounds of formula I, which are representative of the present invention (except for those marked with "*" which are shown for comparative purposes).

TABLE 1

| Example | R¹ | R² | R³ | Ar |
|---|---|---|---|---|
| a | $CH_3$ | $CH_2CH_3$ | $CH_3$ | phenyl |
| b | $NH_2$ | $CH_2CH_3$ | $CH_3$ | phenyl |
| c | $CH_3$ | $CH_2CH_3$ | $CH_3$ | 4-F-phenyl |
| d | $CH_3$ | (S)—$CH_2CH_3$ | $CH_3$ | 4-F-phenyl |
| e | $CH_3$ | (R)—$CH_2CH_3$ | $CH_3$ | 4-F-phenyl |
| f | $CH_3$ | $CH_2CH_3$ | $CH_3$ | 3-F-phenyl |
| g | $CH_3$ | $CH_2CH_3$ | $CH_3$ | 3,4-diF-phenyl |
| h | $CH_3$ | (R)—$CH_2CH_3$ | $CH_3$ | 3,4-diF-phenyl |
| i | $CH_3$ | (S)—$CH_2CH_3$ | $CH_3$ | 3,4-diF-phenyl |
| j | $NH_2$ | $CH_2CH_3$ | $CH_3$ | 3,4-diF-phenyl |
| k | $CH_3$ | $CH_2CH_3$ | $CH_3$ | 4-Cl-phenyl |
| l | $CH_3$ | $CH_2CH_3$ | $CH_3$ | 4-Br-phenyl |
| m | $CH_3$ | $CH_2CH_2CH_3$ | $CH_3$ | phenyl |

TABLE 1-continued

[Structure: furanone with R2, R3 at 5-position, Ar at 3-position, and 4-(SO2R1)phenyl at 4-position]

| Example | R¹ | R² | R³ | Ar |
|---|---|---|---|---|
| n | CH₃ | CH₂CH₂CH₃ | CH₃ | 4-F-phenyl |
| o | CH₃ | CH₂CH₂CH₃ | CH₃ | 3-F-phenyl |
| p | CH₃ | CH₂CH₂CH₃ | CH₃ | 3,4-diF-phenyl |
| q | NH₂ | CH₂CH₂CH₃ | CH₃ | 4-F-phenyl |
| r | NH₂ | CH₂CH₂CH₃ | CH₃ | 3,4-diF-phenyl |
| s | CH₃ | CH(CH₃)₂ | CH₃ | 4-F-phenyl |
| t* | CH₃ | CH₂CH₃ | CH₂CH₃ | phenyl |
| u* | CH₃ | CH₂CH₃ | CH₂CH₃ | 4-F-phenyl |
| v* | NH₂ | CH₂CH₃ | CH₂CH₃ | phenyl |
| w* | NH2 | CH₂CH₃ | CH₂CH₃ | 4-F-phenyl |
| x | CH₃ | CH₂CH₃ | CF₃ | 3,4-diF-phenyl |
| y | CH₃ | CH₂CH₃ | CH₂F | 3,4-diF-phenyl |
| z | CH₃ | CH₂CH₃ | CHF₂ | 3,4-diF-phenyl |
| aa | CH₃ | CH₂CH₃ | CH₃ | 2-pyridyl |
| bb | CH₃ | CH₂CH₃ | CH₃ | 3-pyridyl |
| cc | CH₃ | CH₂CH₃ | CH₃ | 4-pyridyl |
| dd | CH₃ | cyclopropyl | CH₃ | 3,4-diF-phenyl |
| ee | CH₃ | CH₂-cyclopropyl | CH₃ | 4-F-phenyl |

Compounds of Formula I can be tested using the following assays to determine their COX-2 inhibiting activity.

INHIBITION OF CYCLOOXYGENASE ACTIVITY

Whole cell assays for COX-2 and COX-1 using CHO transfected cell lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300 x g, 10 min) and washed once in HBSS containing 15 mM HEPES, pH 7.4, and resuspended in HBSS, 15 mM HEPES, pH 7.4, at a cell concentration of $1.5 \times 10^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells ($0.3 \times 10^6$ cells in 200 µl) are preincubated with 3 µl of the test drug or DMSO vehicle for 15 min at 37° C. Working solutions of peroxide-free AA (5.5 µM and 110 µM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 µM AA in the CHO[hCOX-1] assay and a final concentration of 10 µM AA in the CHO[hCOX-2] assay. The reaction is terminated by the addition of 10 µl 1 N HCl followed by neutralization with 20 µl of 0.5 N NaOH. The samples are centrifuged at 300 x g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 cell microsomes

U 937 cells are pelleted by centrifugation at 500 x g for 5 min and washed once with phosphate-buffered saline and repelleted. Cells are resuspended in homogenization buffer consisting of 0.1 M Tris-HCl, pH 7.4, 10 mM EDTA, 2 µg/ml leupeptin, 2 µg/ml soybean trypsin inhibitor, 2 µg/ml aprotinin and 1 mM phenyl methyl sulfonyl fluoride. The cell suspension is sonicated 4 times for 10 sec and is centrifuged at 10,000 x g for 10 min at 4° C. The supernatant is centrifuged at 100,000 x g for 1 hr at 4° C. The 100,000 x g microsomal pellet is resuspended in 0.1 M Tris-HCl, pH 7.4, 10 mM EDTA to approximately 7 mg protein/mil and stored at $-80°$ C.

Microsomal preparations are thawed immediately prior to use, subjected to a brief sonication, and then diluted to a protein concentration of 125 µg/ml in 0.1 M Tris-HCl buffer, pH 7.4 containing 10 mM EDTA, 0.5 mM phenol, 1 mM reduced glutathione and 1 µM hematin. Assays are performed in duplicate in a final volume of 250 µl. Initially, 5 µl of DMSO vehicle or drug in DMSO are added to 20 µl of 0.1 M Tris-HCl buffer, pH 7.4 containing 10 mM EDTA in wells of a 96-deepwell polypropylene titre plate. 200 µl of the microsomal preparation are then added and pre-incubated for 15 min at room temperature before addition of 25 µl of 1 M arachidonic acid in 0.1 M Tris-HCl and 10 mM EDTA, pH 7.4. Samples are incubated for 40 min at room temperature and the reaction is stopped by the addition of 25 µl of 1 N HCl. Samples are neutralized with 25 µl of 1 N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2 (Copeland et al. (1994) *Proc. Natl. Acad. Sci.* 91, 11202–11206).

Recombinant human COX-2 is purified from Sf9 cells as previously described (Percival et al. (1994) *Arch. Biochem. Biophys.* 15, 111–118). The assay mixture (180 µL) contains 100 mM sodium phosphate, pH 6.5, 2 mM genapol X-100, 1 µM hematin, 1 mg/ml gelatin, 80–100 units of purified enzyme (One unit of enzyme is defined as the amount of enzyme required to produce an O.D. change of 0.001/min at 610 nm) and 4 µL of the test compound in DMSO. The mixture is pre-incubated at room temperature (22° C.) for 15 minutes prior to initiation of the enzymatic reaction by the addition of 20 µL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D. /min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane B2 ($TXB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_9$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 µg/ml final concentration, Sigma Chem, #L-2630 from *E. coli*; diluted in 0.1% BSA (Phosphate buffered saline) for 5 minutes at room temperature. Five hundred µL aliquots of blood are incubated with either 2 µL of vehicle (DMSO) or 2 µL of a test compound at final concentrations varying from 10 nM to 30 µM for 24 hours at 37° C. At the end of the incubation, the blood is centrifuged at 12,000 x g for 5 minutes to obtain plasma. A 100 µL aliquot of plasma is mixed with 400 µL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000 x g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_O$) is measured using a plethysmometer (Ugo-Basile, Italy) based on the principle of water displacement. The animals are then injected subplantarly with 50 μl of 1% carrageenan solution in saline (FMC Corp, Maine) into the paw using an insulin syringe with a 25-gauge needle (i.e. 500 μg carrageenan per paw). Three hr later, the paw volume ($V_3$) is measured and the increases in paw volume ($V_3$–$V_O$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 μCi of sodium $^{51}$chromate for 30 min. at 37° C. At the end of the incubation, the red blood cells are washed twice with 20 μL HBSS to remove free sodium $^{51}$chromate. The red blood cells are finally reconstituted in 10 mL HBSS and 0.5 mL of the solution (about 20 μCi) is injected per rat.

PROTEIN-LOSING GASTROPATHY IN SQUIRREL MONKEYS

Protein-losing gastropathy (manifested as appearance of circulating cells and plasma proteins in the GI tract) is a significant and dose-limiting adverse response to standard non-steroidal antiinflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 μCi/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

LPS-Induced Pyrexia in Conscious Rats

Male Sprague-Dawley rats (150–200 g) were fasted for 16–18 h before use. At approximately 9:30 a.m., the animals were placed temporarily in plexiglass restrainers and their baseline rectal temperature was recorded using a flexible temperature probe (YSI series 400) connected to a digital thermometer (Model 08502, Cole Parmer). The same probe and thermometer were used for all animals to reduce experimental error. The animals were returned to their cages after the temperature measurements. At time zero, the rats were injected intraperitoneally with either saline or LPS (2 mg/kg, Sigma Chem) and the rectal temperature was remeasured at 5, 6 and 7 h following LPS injection. After the measurement at 5 h, when the increase in temperature had reached a plateau, the LPS-injected rats were given either the vehicle (1% methocel) or a test compound orally to determine whether the compound could reverse the pyrexia. Percent reversal of the pyrexia was calculated using the rectal temperature obtained at 7 h in the control (vehicle-treated) group as the reference (zero reversal) point. Complete reversal of pyrexia to the pre-LPS baseline value is taken as 100%.

LPS-Induced Pyrexia in Conscious Squirrel Monkeys

Temperature probes were surgically implanted under the abdominal skin in a group of squirrel monkeys (Saimiri sciureus) (1.0–1.7 kg). This allows for the monitoring of body temperature in conscious, unrestrained monkeys by a telemetric sensing system (Data Sciences International, Minnesota). The animals were fasted and were placed in individual cages for acclimatization 13–14 h before use. Electronic receivers were installed on the side of the cages which pick up signals from the implanted temperature probes. At approximately 9:00 a.m. on the day of the experiment, the monkeys were restrained temporarily in training chairs and were given a bolus I.V. injection of LPS, (6 mg/kg, dissolved in sterile saline). The animals were returned to their cages and body temperature was recorded continuously every 5 min. Two h after injection of LPS, when the body temperature had increased by 1.5–2° C., the monkeys were dosed orally with either vehicle (1% methocel) or a test compound (3 mg/kg). One hundred minutes later, the difference between the body temperature and the baseline value was determined. Percent inhibition was calculated taking the value in the control group as 0% inhibition.

Acute Inflammatory Hyperalgesia Induced by Carrageenan in Rats

Experiments were performed using male Sprague Dawley rats (90–110g). Hyperalgesia to mechanical compression of the hind paw was induced by intraplantar injection of carrageenan (4.5 mg into one hind paw) 3 h previously. Control animals received an equivalent volume of saline (0.15 ml intraplantar). A test compound (0.3–30 mg/kg, suspended in 0.5% methocel in distilled water) or vehicle (0.5% methocel) was administered orally (2 ml/kg) 2 h after carrageenan. The vocalisation response to compression of the hind paw was measured 1 h later using a Ugo Basile algesiometer.

Statistical analysis for carrageenan-induced hyperalgesia was performed using one-way ANOVA (BMDP Statistical Software Inc.). Hyperalgesia was determined by subtracting the vocalisation threshold in saline injected rats from that obtained in animals injected with carrageenan. Hyperalgesia scores for drug-treated rats were expressed as a percentage of this response. $ID_{50}$ values (the dose producing 50% of the maximum observed response) were then calculated by non-linear least squares regression analysis of mean data using GraFit (Erithacus Software).

Adjuvant-Induced Arthritis in Rats

Seventy, 6.5–7.5 week old, female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 ml of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day −1) and 21 days following adjuvant injection, and primary paw volumes were determined before (day −1) and on days 4 and 21 following adjuvant injection. The rats were anesthetized with an intramuscular injection of 0.03–0.1 ml of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, Indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

Two-factor ('treatment' and 'time') analysis of variance with repeated measures on 'time' were applied to the % changes for body weight and foot volumes and to the rank-transformed radiographic total scores. A post hoc Dunnett's test was conducted to compare the effect of treatments to vehicle. A one-way analysis of variance was applied to the thymic and spleen weights followed by the Dunnett's test to compare the effect of treatments to vehicle. Dose-response curves for % inhibition in foot volumes on days 4, 14 and 21 were fitted by a 4-parameter logistic function using a non-linear least squares' regression. $ID_{50}$ was defined as the dose corresponding to a 50% reduction from the vehicle and was derived by interpolation from the fitted 4-parameter equation.

PHARMACOKINETICS IN RATS

Per Os Pharmacokinetics in Rats—Procedure:

The animals are housed, fed and cared for according to the Guidelines of the Canadian Council on Animal Care. Male Sprague Dawley rats (325–375 g) are fasted overnight prior to each PO blood level study. The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparirnized vacutainer tube.

Compounds are prepared as required, in a standard dosing volume of 10 mL/kg, and administered orally by passing a 16 gauge, 3" gavaging needle into the stomach. Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed. Typical time points for determination of rat blood levels after PO dosing are 0, 15 min, 30 min, 1 h, 2 h, 4 h, and 6 h.

After the 4 hr time point bleed, food is provided to the rats ad libitum. Water is provided at all times during the study.

The following vehicles may be used in PO rat blood level determinations:

PEG 200/300/400: restricted to 2 mL/kg

Methocel 0.5%–1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug.

Intravenous Pharmacokinetics in Rats—Procedure

The animals are housed, fed and cared for according to the Guidelines of the Canadian Council on Animal Care. Male Sprague Dawley (325–375 g) rats are placed in plastic shoe box cages with a suspended floor, cage top, water bottle and food. The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes. Typical time points for determination of rat blood levels after I.V. dosing are either a) 0, 5 min, 15 min, 30 min, 1 h, 2 h, 6 h, or b) 0, 5 min, 30 min, 1 h, 2 h, 4 h, 6 h.

The following vehicles may be used in IV rat blood level determinations:

Dextrose: 1 mL/kg

Moleculosol 25%: 1 mL/kg

DMSO (dimethylsulfoxide): Restricted to a dose volume of 0.1 mL per animal

PEG 200: Not more than 60% mixed with 40% sterile water —1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h•kg (milliliters per hour kilogram)

Compounds of the present invention are inhibitors of COX-2 and are thereby useful in the treatment of COX-2 mediated diseases as enumerated above. The activities of the compounds against cyclooxygenase may be seen in the representative results shown below. In the assay, inhibition is determined by measuring the amount of prostaglandin $E_2$ (PGE$_2$) synthesized in the presence of arachidonic acid, COX-1 or COX-2 and a putative inhibitor. The $IC_{50}$ values represent the concentration of putative inhibitor required to lower PGE$_2$ synthesis to 50% of that obtained as compared to the uninhibited control.

The following Tables illustrate the in vitro activity, COX-1/COX-2 selectivity and a pharmacokinetic parameter, the half-life in rats. These data are required to show the advantage of the claimed class of compounds.

Table 2 consists of selected examples showing good in vitro activity, and half-lives in rats ranging from 1 h to 5 h.

Compounds shown in Table 3 are comparison compounds having similar in vitro activity to the class described in Table 2 but have extended half-lives in rats of >24. Compound T3-1 is 3-(4-fluorophenyl)-5,5-dimethyl-4-[4-(methylsulfonyl)phenyl]-2,5-dihydro-2-furanone (WO 95/00501, Example 12), and compound T3-2 is 3-(3,4-difluorophenyl)-5,5-dimethyl-4-[4-(methylsulfonyl)phenyl]-2,5-dihydro-2-furanone (WO95/00501, Example 58).

Therefore the class of compounds described in Table 2 will provide therapeutic benefits similar to the class of compounds described in Table 3 but without the possible adverse effects associated with long lasting (or unmetabolised) drugs. In general, it is undesirable to have a foreign agent in circulation for longer than is necessary to accomplish its beneficial mission. And in particular, should any toxicity due to a medication be manifested in a particular patient, a prolonged half-life would result in on-going exposure to the detrimental effects, and thus would increase the risk/benefit ratio. A half-life of under 24 h also permits a more rapid, deliberate and controllable variation of the dose level in patients than would be possible with a medication with a much longer half-life. It is to be noted that the vast majority of the currently used antiinflammatory and analgesic agents have half-lives of less than 24 h (see A. Mukherjee et al. *Inflamm. Res.* vol. 45, pp. 531–540 (1996)).

Table 4 consists of compounds wherein $R^2=R^3=Et$. They are listed for comparative purposes to illustrate the superior in vitro activity of compounds from Table 2 over compounds in which $R^2=R^3$.

The results for inhibition of PGE$_2$ production may be seen in the following tables (compound references are from Table 1):

Biological activity of compounds of the present invention

TABLE 2

| Compound | CHO Cox-2 (μM) | HWB Cox-2 (μM) | U937 Cox-1 (μM) | HWB Cox-1 (μM) | T 1/2 in Rats (h) |
|---|---|---|---|---|---|
| a |  | <0.37 | 3–10 | >30 |  |
| c | 0.022 | 0.59 | 7.4 | >30 | 3 |
| d | 0.057 | 0.31 | 3.2 | 8.3 |  |
| e | 0.020 | 0.13 | 6.2 | 46 |  |
| f |  | 0.48 | >10 | >30 |  |
| h | 0.051 | 1.55 | 24.8 | 76 | 3.6 |
| i | 0.042 | 0.53 | 13.4 | 46.4 | 4.8 |
| n | 0.194 | 2.51 | >10 | >90 | ~1 |
| o | 0.692 | 3.55 | >10 |  |  |
| p | 0.237 | 2.44 | >10 |  |  |

TABLE 3

Comparison Compounds

| Compound | CHO Cox-2 (μM) | HWB Cox-2 (μM) | U937 Cox-1 (μM) | HWB Cox-1 (μM) | T 1/2 in Rats (h) |
|---|---|---|---|---|---|
| T3-1 | 0.042 | <0.37 | 5.8 | 86.1 | >24 |
| T3-2 |  |  | 10–30 | >30 | >24 |

Comparison compounds u and v show the following ativities

TABLE 4

Comparison Compounds

| Compound | CHO Cox-2 (μM) | HWB Cox-2 (μM) | U937 Cox-1 (μM) |
|---|---|---|---|
| t | >5 | 12.2 | >10 |
| u | >5 | 13.9 | >10 |

The invention will now be illustrated by the following non-limiting examples in which, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (millilitres), g (gram (s)), mg (milligrams(s)), mol (moles), mmol (millimoles), eq (equivalent(s)).

EXAMPLE 1

5-Ethyl-5-methyl-4-[4-(methylsulfonyl)phenyl]-3-phenyl-2,5-dihydro-2-furanone

Step 1: 2-methyl-1-[4-(methylthio)phenyl]-1-butanone

A 500 mL RBF equipped with a mechanical stirrer was charged with $AlCl_3$ (35.4 g) and $CHCl_3$ (300 mL) and cooled in an ice bath. Then 2-methylbutanoyl chloride (31.4 g) was added over 0.5 h to the ice-cold suspension. Keeping the internal temperature <10° C., thioanisole (31.2 mL) was added dropwise over 1 h. After completion of addition, the resulting mixture was stirred at r.t. for 2 h. The resulting suspension was poured onto an ice-water mixture and stirred until decoloraton. The organic layer was separated, washed with water, dried over $Na_2SO_4$ and concentrated to dryness. The resulting white solid was swished in hexane and collected by filtration to give the title compound as a white solid. $^1H$ NMR($CD_3COCD_3$): δ0.88 (3H, t), 1.12 (3H, d), 1.47 (1H, m), 1.78 (1H, m), 2.57 (3H, s), 3.49 (1H, m), 7.37 (2H, d), 7.93 (2H, d).

Step 2: 2-Hydroxy-2-methyl-1-[4-(methylthio)phenyl]-1-butanone

To a solution of the ketone from step 1 (33 g) in toluene (48 mL), $CCl_4$ (23.5 mL) and Aliquat, 336 (10.5 mL), was added NaOH pellets (14.5 g) and the resulting mixture was vigorously stirred for 2 days. The reaction mixture was diluted with 5N HCl, aqueous $NH_4Cl$ and extracted with $Et_2O$. The organic layer was dried over $Na_2SO_4$ and concentrated. The crude product was purified by flash chromatography eluted with EtOAc/Hexane 9% to give a yellow syrup.

Step 3: 2-Hydroxy-2-methyl-1-[4-(methylsulfonyl)phenyl]-1-butanone

To an ice-cold solution of the methylthio compound obtained from step 2 (21.0 g) in $CH_2Cl_2$ (315 mL) and MeOH (35 mL) was added MMPP (54.0 g of 80% pure). The resulting mixture was stirred at r.t. for 40 min. The reaction was diluted with $CH_2Cl_2$ (200 mL) filtered through silica gel, and washed with $NaHCO_3$ (200 mL). The mixture was shaken vigorously, layers separated, the organic layer was dried over $MgSO_4$ and concentrated to give a yellow syrup which was used without purification.

Step 4: 1-Methyl-1-[4-(methylsulfonyl)benzoyl]propyl-2-phenylacetate

A mixture of tertiary alcohol from Step 3 (2.13 g), phenyl acetic acid (4.3 g), 1-cyclohexyl-3-(2-morpholinoethyl) carbodiimide metho-p-toluenesulfonate (9.8 g) and DMAP (0.41 g) in $CH_2Cl_2$ (50 mL) was heated at 60° C. for 2 h. The reaction mixture was allowed to cool to r.t., diluted with EtOAc (250 mL) and washed twice with aqueous $NaHCO_3$. The organic layer was dried over $MgSO_4$ and concentrated. The resulting crude product was purified by flash chromatography. (40%→50% ETOAc in hexane) to give a colorless gum.

Step 5: 5-Ethyl-5-methyl-4-[4-(methylsulfonyl)phenyl]-3-phenyl-2,5-dihydro-2-furanone To an ice-cold solution of the ester from step 4 (2.5 g) in acetonitrile (60 mL) was added DBU (1.5 mL) over 3 min. and the resulting mixture was stirred at r.t. for 2 h. Solvents were removed under reduced pressure and the resulting residue was applied as such on a flash chromatography column (40%→50%→60% EtOAc in hexane) and then crystallized in 40 mL of 1:2 EtOAc/hexane to give white needles. $^1H$ NMR($CD_3COCD_3$): δ0.98 (3H, t), 1.63 (3H, s), 1.96 (2H, m), 3.16 (3H, s), 7.29 (2H, m), 7.35 (2H, m), 7.63 (2H, d), 8.02 (2H, d).

EXAMPLE 2

5-Ethyl-3-(4-fluorophenyl)-5-methyl-4-[(methylsulfonyl) phenyl]-2,5-dihydro-2-furanone Using the procedures described in example 1 and replacing in Step 4 phenylacetic acid with p-fluorophenylacetic acid, the title compound was obtained as a white solid. $^1H$ NMR($CD_3COCD_3$): δ0.98 (3H, t), 1.63 (3H, s), 1.96 (2H, m), 3.17 (3H, s), 7.06 (2H, t), 7.41 (2H, dd), 7.64 (2H, d), 8.04 (2H, s).

EXAMPLE 3

(5R)-5-Ethyl-3-(4-fluorophenyl)-5-methyl-4-[4-(methyl-sulfonyl)phenyl ]-2.5-dihydro-2-furanone Step 1: (2S,5S)-2-(tert-butyl)-5-methyl-1,3-dioxolan-4-one A mixture of L-Lactic acid (106 g of 85% in $H_2O$), pivalaldehyde (220 mL), p-toluene sulfonic acid mono hydrate (2.0 g) and $H_2SO_4$ conc. (8 drops) in pentane (800 mL) was refluxed with azeotropic removal of the water formed using a Dean-Stark trap. The supernatant was decanted, washed with water, dried over $MgSO_4$ and concentrated. The resulting residue was dissolved in hexane (800 mL) and cooled to −80° C. for 20 h. Crystals were collected by filtration in a cold room (5° C.) and washed with cold hexane (−78° C.). The crystals were dissolved in $Et_2O$, dried over $MgSO_4$ and concentred to give the title compound as a colorless oil. $^1H$ NMR($CD_3COCD_3$): δ0.95 (9H, s), 1.38 (3H,d), 4.47 (1H, m), 5.24 (1H, s).

Step 2: (2S,5R)-2-(tert-butyl)-5-ethyl-5-methyl-1,3-dioxolan-4-one

To a solution of diisopropylamine (44 mL) in THF (700 mL) at −30° C. was added a solution of 1.6M n-butyllithium in hexane (190 mL). The resulting solution was stirred at −10° C. for 30 min. and cooled to −78° C. Then a solution of dioxolanone obtained from Step 1 (44.5 g) in THF (100 mL) was added to the reaction mixture with a double-tipped needle.

After 1.5 h, iodoethane (33 mL) was added. The reaction mixture was stirred at −78° C. for 1 h and then allowed to warm to −10° C. over 1 h. The reaction mixture was diluted with half-saturated aqueous NH$_4$Cl (1 L) and extracted with EtOAc (1 L). The organic layer was washed with brine, dried over MgSO$_4$ and concentrated. The crude product was purified by distillation. Fraction passing at 85–92° C./10 mm Hg was collected (litt. 110/16 mm Hg) $^1$H NMR (CD$_3$COCD$_3$); δ94 (9H, s), 0.97 (3H, t), 1.37 (3H, s), 1.77 (2H, m), 5.29 (1H, s).

Step 3: (2S,5S)-2-(tert-butyl)-5-ethyl-5-methyl-4-[4-(methylthio) phenyl]-1,3-dioxolan-4-ol A solution of 4-bromothioanisole (48.5 g) in THF (600 mL) was cooled to −70° C. and a 2.5M solution of n-butyllithium in hexane (96 mL) was slowly added over 20 min. The resulting suspension was stirred for 1 h allowing the temperature of the cooling bath to raise to −50° C. It was then cooled back to −70° C. and a solution of dioxolanone from Step 2 (29.8 g) in TBF (100 mL) was added dropwise over 30 min. The reaction was allowed to proceed for another 30 min. and then quenched with AcOH (23 mL) always at −70° C. The reaction mixture was allowed to warm to r.t., diluted with a 25% aqueous solution of NH$_4$OAc and extracted with EtOAc (2 L). The organic layer was dried over MgSO$_4$ and concentrated. The resulting crude product was purified by flash chromatography (2→3→5→7% EtOAc in hexane) to give a light yellow solid. $^1$H NMR (CD$_3$COCD$_3$): mixture of diastereomers δ0.50 (0.5H, m), 0.68 (1.5H, s), 0.72 (1.5H, t), 0.97 (1.5H, t), 0.98 (9H, s), 1.38 (1.5H, s), 1.52 m), 1.68 (0.5H, m), 2.10 (0.5H, m), 2.48 (3H, 2s), 4.85 (1H, s, OH), 5.01 (0.5H, s), 5.32 (0.5H, s), 7.22–7.30 (2H, m), 7.50 (2H, dd).

Step 4: (2R)-2-Hydroxy-2-methyl-1-[4-(methylsulfonyl)phenyl]butan-1-one

A mixture of the dioxolanol from Step 3 (46.2 g) in water (50 mL) with p-toluenesulfonic acid mono hydrate (1.3 g) was refluxed for 1 hour. The reaction was allowed to cool to r.t. and extract twice with EtOAc (200+150 mL). To this solution was added t-BuOH (175 mL) and Aliquat® 336. This solution was cooled to 10° C. and then a solution of OXONE® (130 g) in water (800 mL) was added over 30 min. The resulting mixture was stirred at r.t. for 20 h. The reaction mixture was neutralized by carefull and portionwise addition of aqueous saturated NaHCO$_3$ and extracted with EtOAc. The organic layer was dried over MgSO$_4$ and concentrated to give a yellow syrup. $^1$H NMR(CD$_3$COCD$_3$): δ0.90 (3H, t), 1.49 (3H, s), 1.81 (1 H, m), 1.95 (1H, s, OH), 1.99 (1H, m), 3.17 (3H, s), 8.02 (2H, d), 8.32 (2H, d).

Step 5: (5R)-5-Ethyl-3-(4-fluorophenyl)-5-methyl-4-[4-(methylsulfonyl)phenyl ]-2,5-dihydro-2-furanone Using the procedures described in Example 1, Step 4 and Step 5, replacing phenylacetic acid with p-fluorophenylacetic acid and replacing 2-hydroxy-2-methyl-1-[4-(methylsulfonyl)phenyl]-1-butanone with (2R)-2-hydroxy-2-methyl-1-[4-(methylsulfonyl)phenyl] butan-1-one from Step 4, the title compound was obtained as a white solid.

M.S. (+APCI) m/z 375 (M +H)$^+$, [α]$_D$+32° (c=1.0, acetone), m.p. 120–121° C.

EXAMPLE 4

(5S)-5-Ethyl-3-(4-fluorophenyl)-5-methyl-4-[4-(methyl-sulfonvl)phenyl ]-2,5-dihydro-2-furanone Using the procedure described in Example 3, Step 5 and replacing (2R)-2-hydroxy-2-methyl-1-[4-(methylsulfonyl) phenyl ]butan-1-one with (2S)-2-hydroxy-2-methyl-1-[-(methyl-sulfonyl)phenyl ]butan-1-one the title compound was obtained as a white solid. M.S. (CI, CH$_4$) m/z 375 (M+H)$^+$,[α]$_D$−33° (C=1.0, acetone), m.p. 119–120° C.

EXAMPLE 5

5-Ethyl-3-(3-fluorophenyl)-5-methyl-4-[4-(methylsulfonyl)phenyl]-2,5-dihydro-2-furanone Using the procedures described in Example 1 and replacing in Step 4 phenylacetic acid with m-fluorophenylacetic acid, the title compound was obtained as a white solid. $^1$H NMR(CD$_3$COCD$_3$): δ0.99 (3H, t), 1.64 (3H, s), 1.97 (2H, m), 3.18 (3H, s), 7.14–7.23 (2H, m), 7.20 (1H, d), 7.32 (1H, m), 7.66 (2H, d), 8.05 (2H, d)

EXAMPLE 6

3-(4-fluorophenyl)-5-methyl-4-[4-(methylsulfonyl)phenyl]-5-propyl-2,5-dihydro-2-furanone Using the procedures described in Example 1, replacing in Step 1 2-methylbutanoyl chloride with 2-methylpentanoyl chloride and replacing in Step 4 phenylacetic acid with p-fluorophenylacetic acid, the title compound was obtained as a white solid. M.S. (CI, CH$_4$) m/z 389 (M+H)$^+$, m.p. 112–113° C.

EXAMPLE 7

(5R)-3-(3,4-difluorophenyl)-5-ethyl-5-methyl-4-[4-(methylsulfonyl) phenyl]-2,5-dihydro-2-furanone Using the procedures described in Example 3 and replacing in Step 5 p-fluorophenylacetic acid with 3,4-difluorophenylacetic acid, the title compound was obtained as a white solid. m.p. 144° C., [α]$_D$+32.1° (c=1.3, CHCl$_3$).

EXAMPLE 8

(5S)-3-(3,4-difluorophenyl)-5-ethyl-5-methyl-4-[4-(methylsulfonyl)phenyl ]-2.5-dihydro-2-furanone Using the procedure described in Example 4 and replacing p-fluorophenylacetic acid with 3,4-difluorophenylacetic acid, the title compound was obtained as a white solid. m.p. 142–143° C., [α]$_D$−32.7° (c=1.1, CHCl$_3$)

EXAMPLE 9

3-(3,4-difluorophenyl)-5-methyl-4-[4-(methylsulfonyl) phenyl ]5-propyl-2,5-dihydro-2-furanone Using the procedure described in Example 6 replacing p-fluorophenylacetic acid with 3,4-difluorophenylacetic acid, the title compound was obtained as a white solid. M.S. (+APCI) m/z 407 (M+H)$^+$, m.p. 89–90° C.

EXAMPLE 10

3-(3-fluorophenyl)-5-methyl-4-[4-(methylsulfonyl)phenyl-5-propyl-2,5-dihydro-2-furanone Using the procedure described in Example 6 replacing p-fluorophenylacetic acid with m-fluorophenylacetic acid, the title compound was obtained as a white solid. M.S. (CI, CH$_4$) m/z 389 (M+H)$^+$, m.p. 92–93° C.

What is claimed is:

1. A compound of Formula I

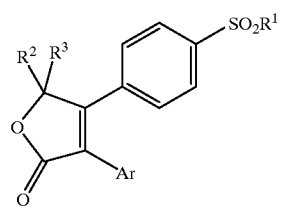

or a pharmaceutically acceptable salt thereof, wherein:

Ar is an unsubstituted, mono or di substituted phenyl or pyridyl, wherein the substituents are selected from halogen;

27

$R^1$ is selected from the group consisting of $NH_2$ and $CH_3$;
$R^2$ is selected from the group consisting of
   $C_{1-6}$ alkyl unsubstituted or substituted with $C_{3-6}$ cycloalkyl, and
   $C_{3-6}$ cycloalkyl;
$R^3$ is selected from the group consisting of
   $C_{1-6}$ alkyl unsubstituted or substituted with one, two or three fluoro atoms; and
   $C_{3-6}$ cycloalkyl;
with the proviso that $R^2$ and $R^3$ are not the same.

2. A compound of claim 1, or a pharmaceutically acceptable salt thereof, wherein Ar is unsubstituted phenyl, phenyl substituted with fluoro, or unsubstituted pyridyl or pyridyl substituted with fluoro.

3. A compound of claim 2, or a pharmaceutically acceptable salt thereof, wherein $R^2$ is $C_{2-3}$ alkyl, $CH_2$-cyclopropyl, or cyclopropyl.

4. A compound of claim 3, or a pharmaceutically acceptable salt thereof, wherein $R^3$ is $CH_3$, $CH_2CH_3$, $CH_2F$, $CHF_2$, or $CF_3$.

5. A compound of claim 4, or a pharmaceutically acceptable salt thereof, wherein $R^3$ is $CH_3$.

6. A compound of claim 4, or a pharmaceutically acceptable salt thereof, selected from the group consisting of
   (a) 5-ethyl-5-methyl-4-[4-(methylsulfonyl)phenyl ]-3-phenyl-2,5-dihydro-2-furanone,
   (b) 4-[4-(aminosulfonyl)phenyl ]-5-ethyl-5-methyl-3-phenyl-2,5-dihydro-2-furanone,
   (c) 5-ethyl-3-(4-fluorophenyl)-5-methyl-4-[4-(methylsulfonyl)phenyl ]-2,5-dihydro-2-furanone,
   (d) (5S)-5-ethyl-3-(4-fluorophenyl)-5-methyl-4-[4-(methylsulfonyl)phenyl ]-2,5-dihydro-2-furanone,
   (e) (5R)-5-ethyl-3-(4-fluorophenyl)-5-methyl-4-[4-(methylsulfonyl)phenyl ]-2,5-dihydro-2-furanone,
   (f) 5-ethyl-3-(3-fluorophenyl)-5-methyl-4-[4-(methylsulfonyl)phenyl ]-2,5-dihydro-2-furanone,
   (g) 3-(3,4-difluorophenyl)-5-ethyl-5-methyl-4-4-(methylsulfonyl)phenyl ]-2,5-dihydro-2-furanone,
   (h) (5R)-3-(3,4-difluorophenyl)-5-ethyl-5-methyl-4-[4-(methylsulfonyl)phenyl ]-2,5-dihydro-2-furanone,
   (i) (5S)-3-(3,4-difluorophenyl)-5-ethyl-5-methyl-4-[4-(methylsulfonyl)phenyl ]-2,5-dihydro-2-furanone,
   (j) 4-[4-(aminosulfonyl)phenyl ]-3-(3,4-difluorophenyl)-5-ethyl-5-methyl-2,5-dihydro-2-furanone,
   (k) 3-(4-chlorophenyl)-5-ethyl-5-methyl-4-[4-(methylsulfonyl)phenyl ]-2,5-dihydro-2-furanone,
   (l) 3-(4-bromophenyl)-5-ethyl-5-methyl-4-[4-(methylsulfonyl)phenyl ]-2,5-dihydro-2-furanone,
   (m) 5-methyl-4-[4-(methylsulfonyl)phenyl ]-3-phenyl-5-propyl-2,5-dihydro-2-furanone,
   (n) 3-(4-fluorophenyl)-5-methyl-4-[4-(methylsulfonyl) phenyl ]-5-propyl-2,5-dihydro-2-furanone,
   (o) 3-(3-fluorophenyl)-5-methyl-4-[4-(methylsulfonyl) phenyl ]-5-propyl-2,5-dihydro-2-furanone,

28

(p) 3-(3,4-difluorophenyl)-5-methyl-4-[4-(methylsulfonyl)phenyl ]-5-propyl-2,5-dihydro-2-furanone,
   (q) 4-[4-(aminosulfonyl)phenyl ]-3-(4-fluorophenyl)-5-methyl-5-propyl-2,5-dihydro-2-furanone,
   (r) 4-[4-(aminosulfonyl)phenyl ]-3-(3,4-difluorophenyl)-5-methyl-5-propyl-2,5-dihydro-2-furanone,
   (s) 3-(4-fluorophenyl)-5-isopropyl-5-methyl-4-[4-(methylsulfonyl)phenyl ]-2,5-dihydro-2-furanone,
   (x) 3-(3,4-difluorophenyl)-5-ethyl-4-[4-(methylsulfonyl)phenyl ]-5-(trifluoromethyl)-2,5-dihydro-2-furanone,
   (y) 3-(3,4-difluorophenyl)-5-ethyl-5-(fluoromethyl)-4-[4-(methylsulfony)phenyl ]-2,5-dihydro-2-furanone,
   (z) 5-(difluoromethyl)-3-(3,4-difluorophenyl)-5-ethyl-4-[4-(methylsulfonyl)phenyl ]-2,5-dihydro-2-furanone,
   (aa) 5-ethyl-5-methyl-4-[4-(methylsulfonyl)phenyl ]-3-(2-pyridyl)-2,5-dihydro-2-furanone,
   (bb) 5-ethyl-5-methyl-4-[4-(methylsulfonyl)phenyl ]-3-(3-pyridyl)-2,5-dihydro-2-furanone,
   (cc) 5-ethyl-5-methyl-4-[4-(methylsulfonyl)phenyl ]-3-(4-pyridyl)-2,5-dihydro-2-furanone,
   (dd) 5-cyclopropyl-3-(3,4-difluorophenyl)-5-methyl-4-[4-(methylsulfony)phenyl ]-2,5-dihydro-2-furanone, and
   (ee) 5-(cyclopropylmethyl)-3-(4-fluorophenyl)-5-methyl-4-[4-(methylsulfonyl)phenyl ]-2,5-dihydro-2-furanone.

7. A compound of claim 6, or a pharmaceutically acceptable salt thereof, selected from the group consisting of
   (c) 5-ethyl-3-(4-fluorophenyl)-5-methyl-4-[4-(methylsulfonyl)phenyl ]-2,5-dihydro-2-furanone,
   (d) (5S)-5-ethyl-3-(4-fluorophenyl)-5-methyl-4-[4-(methylsulfonyl)phenyl ]-2,5-dihydro-2-furanone,
   (e) (5R)-5-ethyl-3-(4-fluorophenyl)-5-methyl-4-[4-(methylsulfonyl)phenyl ]-2,5-dihydro-2-furanone,
   (f) 5-ethyl-3-(3-fluorophenyl)-5-methyl-4-[4-(methylsulfonyl)phenyl ]-2,5-dihydro-2-furanone,
   (g) 3-(3,4-difluorophenyl)-5-ethyl-5-methyl-4-[4-(methylsulfonyl)phenyl ]-2,5-dihydro-2-furanone,
   (h) (5R)-3-(3,4-difluorophenyl)-5-ethyl-5-methyl-4-[4-(methylsulfonyl)phenyl ]-2,5-dihydro-2-furanone, and
   (i) (5S)-3-(3,4-difluorophenyl)-5-ethyl-5-methyl-4-[4-(methylsulfony)phenyl ]-2,5-dihydro-2-furanone.

8. A pharmaceutical composition comprising a therapeutically effective amount of a compound of claim 1 and a pharmaceutically acceptable carrier.

9. A method of treating a patient having inflammatory disease susceptible to treatment with a non-steroidal anti-inflammatory agent comprising administering to the patient in need of such treatment a composition of claim 8.

10. A method of treating a patient having cyclooxygenase mediated disease advantageously treated by an active agent that selectively inhibits COX-2 in preference to COX-1 comprising administering to the patient in need of such treatment a composition of claim 8.

* * * * *